United States Patent
Gong et al.

(10) Patent No.: US 11,911,406 B2
(45) Date of Patent: Feb. 27, 2024

(54) PH-RESPONSIVE POLYMER-DRUG CONJUGATES FOR ENHANCED ANTIBACTERIAL EFFICACY

(71) Applicant: Wisconsin Alumni Research Foundation, Madison, WI (US)

(72) Inventors: Shaoqin Gong, Middleton, WI (US); Mingzhou Ye, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 174 days.

(21) Appl. No.: 17/171,463

(22) Filed: Feb. 9, 2021

(65) Prior Publication Data

US 2021/0244752 A1    Aug. 12, 2021

Related U.S. Application Data

(60) Provisional application No. 62/975,582, filed on Feb. 12, 2020.

(51) Int. Cl.
| | | |
|---|---|---|
| *A61K 31/7048* | (2006.01) | |
| *A61K 47/59* | (2017.01) | |
| *A61P 31/04* | (2006.01) | |
| *A61K 31/4409* | (2006.01) | |
| *A61K 31/7056* | (2006.01) | |
| *A61K 31/496* | (2006.01) | |
| *A61K 38/14* | (2006.01) | |
| *A61K 31/426* | (2006.01) | |
| *A61K 31/7036* | (2006.01) | |
| *C08G 69/10* | (2006.01) | |

(52) U.S. Cl.
CPC ........ *A61K 31/7048* (2013.01); *A61K 31/426* (2013.01); *A61K 31/4409* (2013.01); *A61K 31/496* (2013.01); *A61K 31/7036* (2013.01); *A61K 31/7056* (2013.01); *A61K 38/14* (2013.01); *A61K 47/595* (2017.08); *A61P 31/04* (2018.01); *C08G 69/10* (2013.01)

(58) Field of Classification Search
CPC .............. A61K 31/7036; A61K 47/595; A61K 31/7048; A61K 31/426; A61K 31/4409; A61K 31/496; A61K 31/7056; A61K 38/14; A61P 31/04
See application file for complete search history.

(56) References Cited

PUBLICATIONS

Stebbins et al., Advanced Drug Delivery Reviews, 2014, 78, p. 77-87. (Year: 2014).*
Coessens et al., Journal of Controlled Release, 1996, 38, p. 141-150. (Year: 1996).*
Brumbach et al., Bioconjugate Chem., 2010, 21, p. 1753-1761. (Year: 2010).*

* cited by examiner

*Primary Examiner* — Jonathan S Lau
(74) *Attorney, Agent, or Firm* — Foley & Lardner LLP

(57) ABSTRACT

Provided herein are polymer-drug conjugates with enhanced antibacterial efficacy. These conjugates include a polymer comprising a plurality of masked cationic functional groups and an antibiotic drug linked to the cationic polymer by a pH-sensitive linker. The masked cationic functional groups may be converted in aqueous solution to free cationic functional groups faster at a pH below 7 than a pH above 7. The cationic functional groups may be masked as either an uncharged functional group or by an ion pair with a neighboring anionic functional group attached to the polymer. The pH-sensitive linker releases the drug faster in aqueous solution at or below a pre-determined pH value selected from a range of 4.5 to 7 than a pH value above 7.

22 Claims, 8 Drawing Sheets

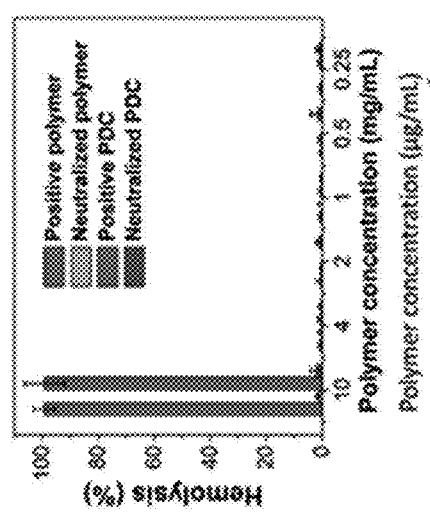
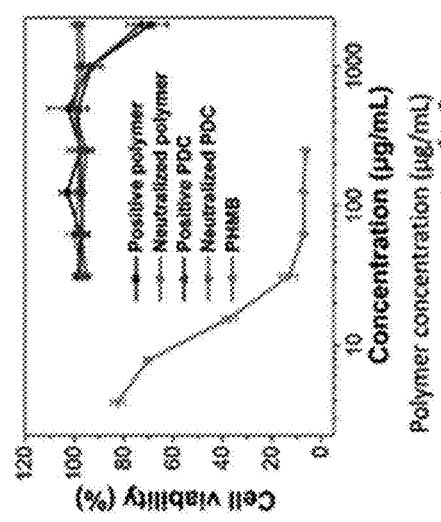
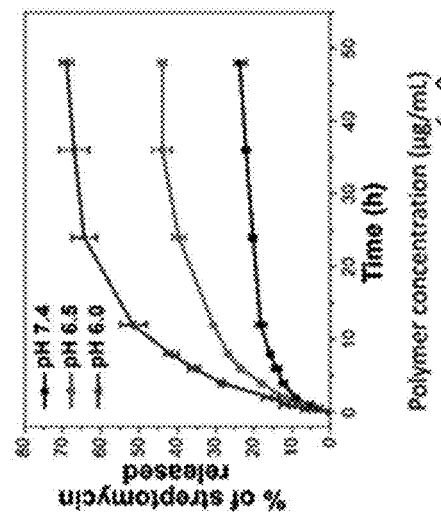
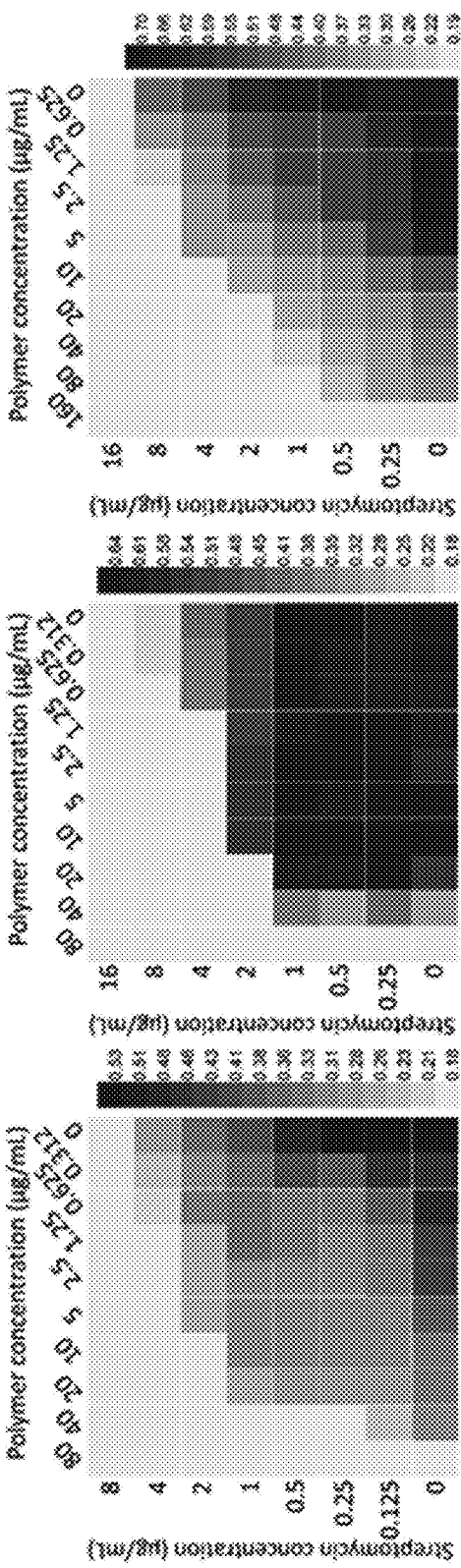

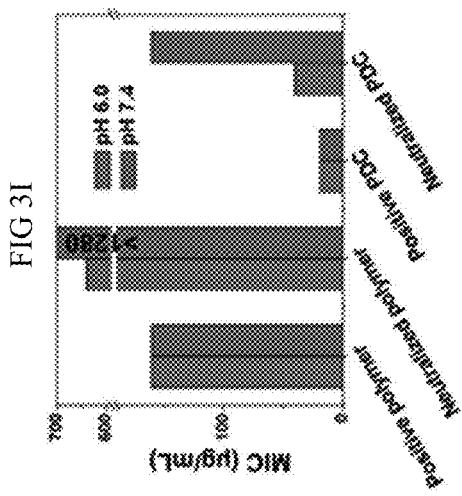
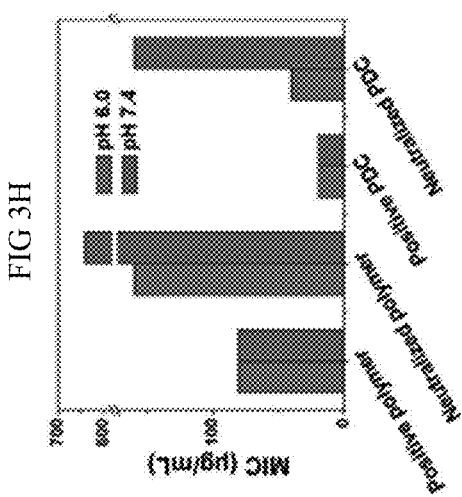
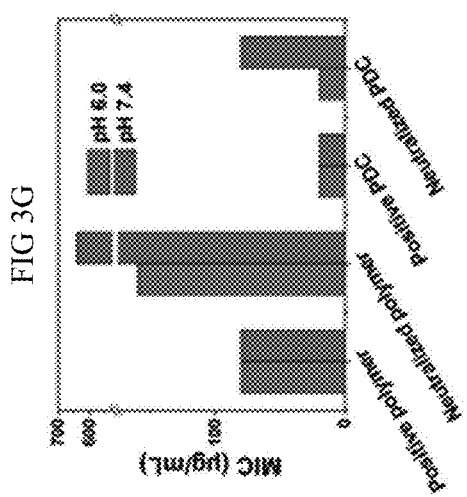

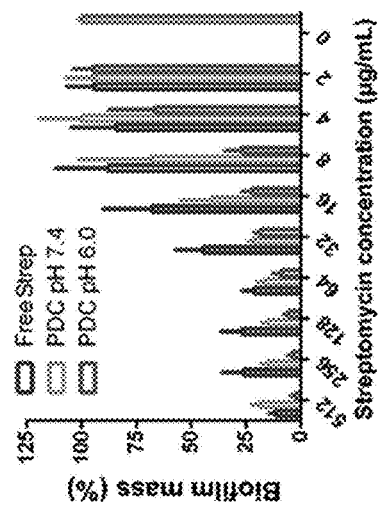
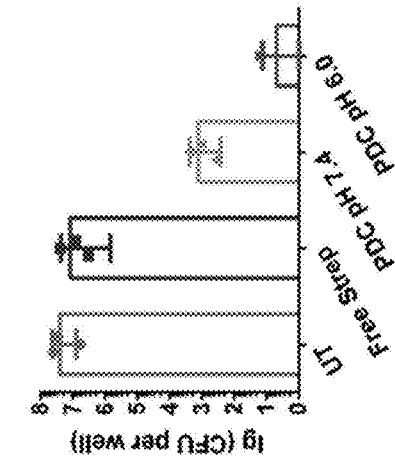
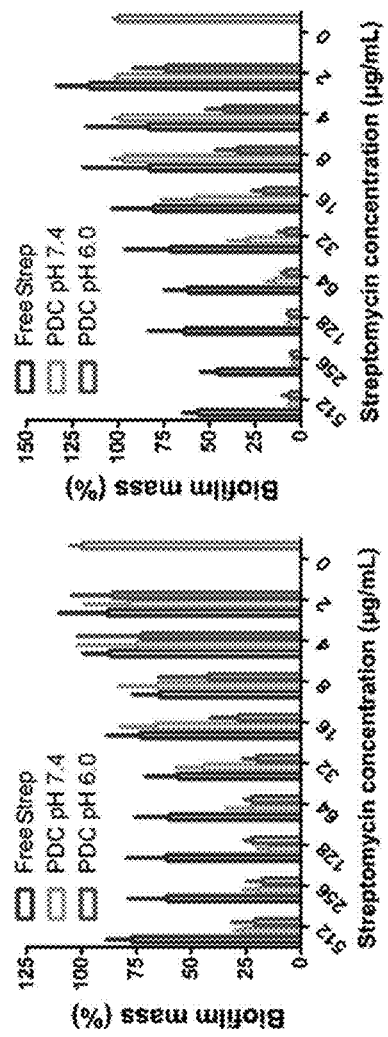
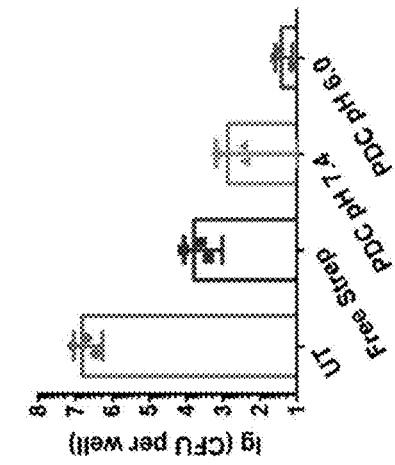
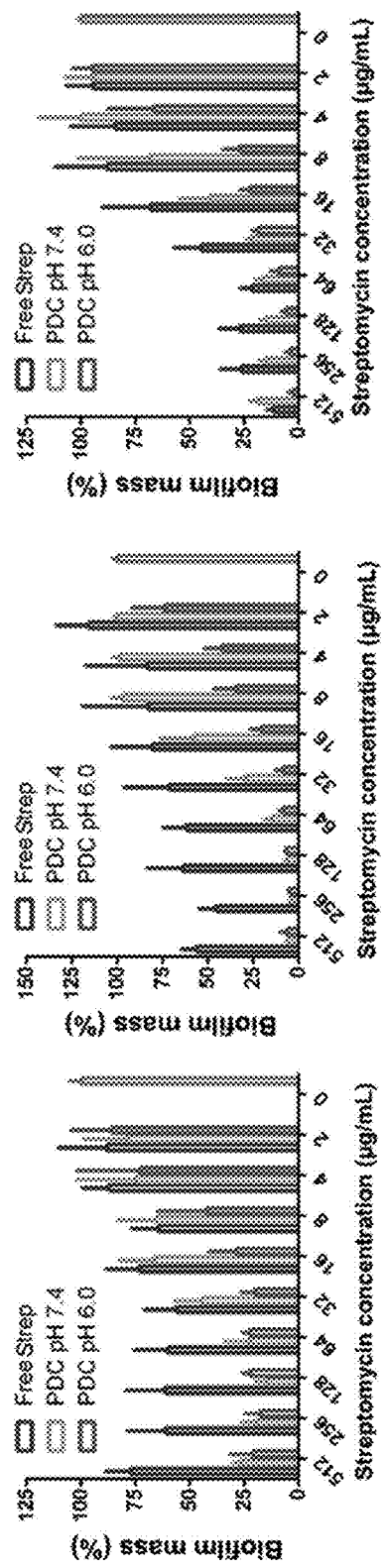
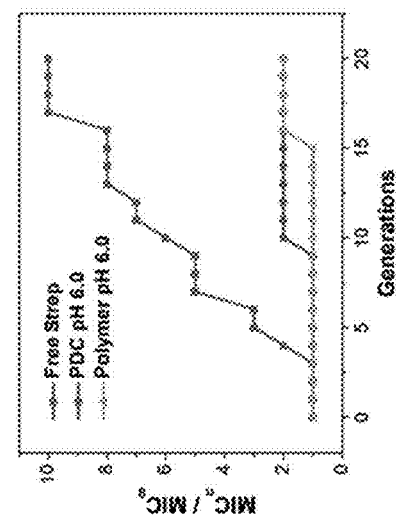

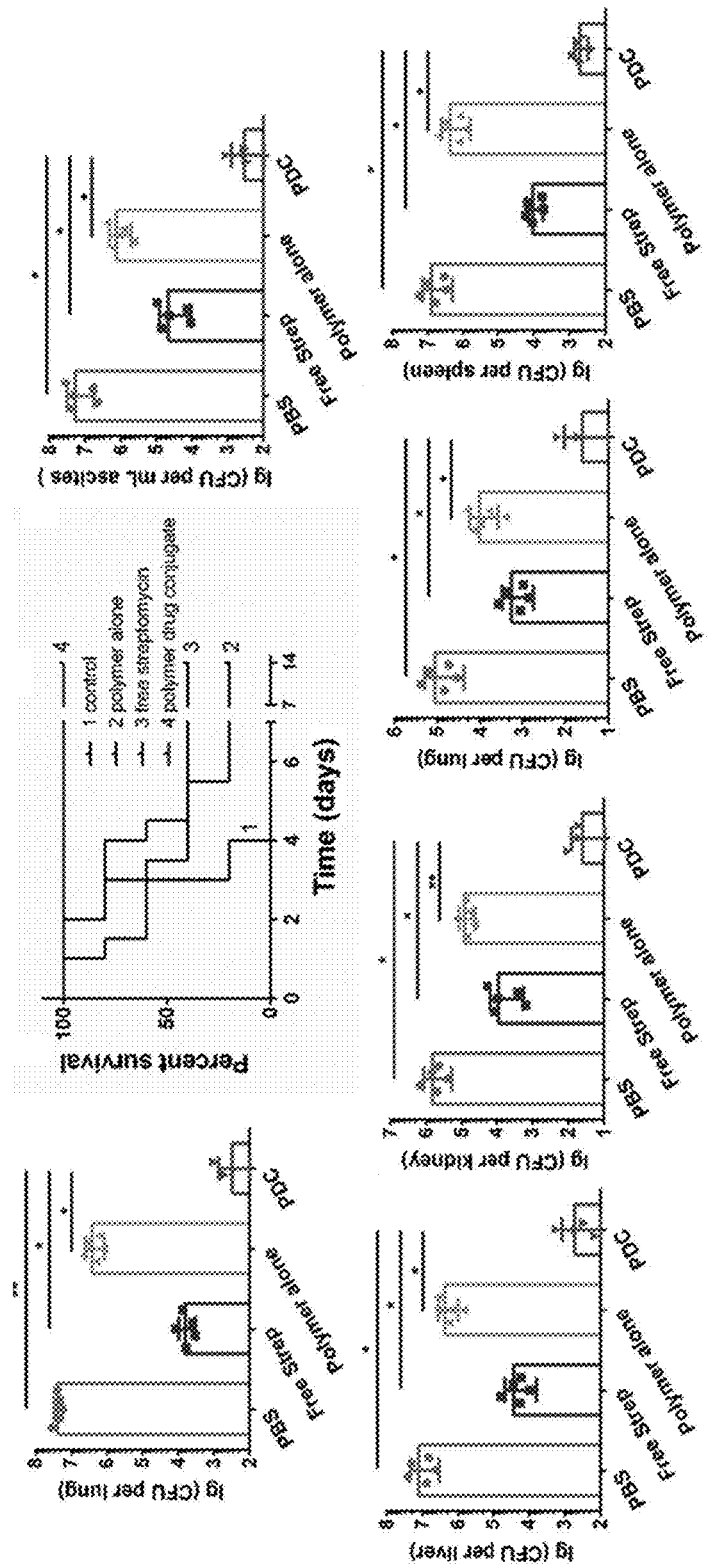

PH-RESPONSIVE POLYMER-DRUG CONJUGATES FOR ENHANCED ANTIBACTERIAL EFFICACY

CROSS REFERENCE TO RELATED APPLICATION

This application claims the benefit of U.S. Provisional Patent Application No. 62/975,582, filed on Feb. 12, 2020, the entire disclosure of which is hereby incorporated by reference for any and all purposes.

FIELD

The present technology relates generally to the field of polymer-drug conjugates for antibacterials drug delivery and enhanced efficacy. The present compositions provide a masked cationic polymer conjugated with a pH-responsive linker to antibacterials that has low toxicity for mammalian cells, but enhanced efficacy against biofilms and drug-resistant organisms.

BACKGROUND

Infectious diseases are a growing threat to public health due to increasing antimicrobial resistance (AMR) and stagnation in new antibiotic development. It is estimated that by the year 2050, AMR infection will be the leading cause of death worldwide and will kill over 10 million people each year if new solutions are not found. The complexity of infection, especially in chronic infectious diseases, necessitates the use of broad-spectrum antibiotics, which drives the selection of drug-resistant pathogens. Furthermore, it is increasingly challenging and costly to develop new antibiotics. In fact, no new class of antibiotics have been developed for treating Gram-negative bacteria caused infections since the 1980s.

AMR can be caused by decreased antibiotic uptake due to reduced permeability, and upregulated efflux pumps that expel the ingested chemicals. Such intrinsic AMR resistance allows the microbes to comprehensively resist various kinds of antibiotic treatments. Biofilms provide further protection to the microorganisms and significantly reduce their susceptibility to antibiotics by building up a resistant microenvironment and rejecting the penetration of the antibacterial agents. Additionally, pathogens can also acquire AMR through enzymatic degradation of antibiotics or alteration of the target proteins.

SUMMARY OF THE INVENTION

The present technology provides a pH-responsive polymer-drug conjugate (also referred to as "PDC" herein) that is capable of treating serious bacterial infections, mitigating and even overcoming bacterial resistance to drugs. The PDC includes a polymer comprising a plurality of masked cationic functional groups wherein the masked cationic functional groups are converted in aqueous solution to free cationic functional groups faster at a pH below 7 than a pH above 7. The cationic functional groups may be masked as either an uncharged functional group or by an ion pair with a neighboring anionic functional group attached to the polymer. The PDC further includes an antibiotic drug linked to the cationic polymer by a pH-sensitive linker that releases the drug faster in aqueous solution at or below a predetermined pH value selected from a range of 4.5 to 7 than a pH value above 7.

BRIEF DESCRIPTION OF THE DRAWINGS

FIGS. 3A-3I show data from an illustrative embodiment of the present technology: (3A) The streptomycin release profiles from a PDC under different pH values. (3B) Cytotoxicity assays of the polymers and PDCs in HEK 293 embryonic human kidney cells for 48 h. Poly(hexamethylene biguanide) (PHMB), a commercially used antibacterial polymer is a positive control. (3C) Hemolysis assay of red blood cells incubated with the polymer and PDC. (3D-F) Checkerboard dilution assays for testing the synergy between the positively-charged polymer and Strep in E. coli (3D), Methicillin-resistant S. aureus (MRSA) (3E), and P. aeruginosa (3F). The scale bars indicate the OD600 in each well 24 h after the treatment. (3G-I) MIC for the polymer and PDC at different pH (6.0 and 7.4) in E. coli (3G), MRSA (3H), and P. aeruginosa (3I).

FIGS. 5A-5F are graphs showing antibacterial effect of PDC with streptomycin under various conditions. FIGS. 5A-C illustrate quantification of biofilm masss of E. coli (5A), MRSA (5B), and P. aeruginosa (5C) treated with streptomycin (Strep) or PDC. FIG. 5D shows the drug resistance development profiles of E. coli (ATCC 25922) during serial passaging in the presence of sub-MIC dosing of Strep, polymer and PDC. The y-axis indicates the fold-increase in MIC compared to the initial MIC. FIGS. 5E-F plot CFUs of intracellular bacteria after different treatments. RAW 264.7 macrophage was seeded in 96-well plate and infected by MRSA (5E) and P. aeruginosa (5F). After removing planktonic bacteria, the cells were treated with strep or PDC for 1 day, and then lysed by Milli-Q water containing 0.1% Triton X-100 (lyses the macrophages without damaging the bacteria). CFU in each well was determined by serial dilution.

FIGS. 6A-L show data from in vivo use of PDC. FIG. 6A shows fluorescence images of a mouse with MRSA infection on its right thigh. Cy5 labeled PDC was given through intravenous injection. The uninfected left thigh is a negative control. FIG. 6B shows an ex vivo fluorescence image for the major organs and tissues of the MRSA infected mouse 24 h after the treatment. Labels H, L, S, Lu, K, I and U represent heart, liver, spleen, lung, kidney, MRSA-infected thigh and the uninfected thigh. FIG. 6C shows a statistical comparison of fluorescent intensity in MRSA-infected leg over the uninfected leg at various time points. FIG. 6D shows a quantitative analysis of the mean fluorescent intensity in each organ or tissue from the ex vivo image. (n=3) FIG. 6E shows the bacterial burden of mice with E. coli thigh infection. A single injection of different treatments (PBS, free strep, polymer alone and PDC) was given intravenously 1 h after the infection. The infected thighs were collected 24 h after the injection, homogenized and total CFU were determined through serial dilution. In vivo efficiency of PDC treatments in a *P. aeruginosa* lung infection mouse model are shown in FIGS. 6F-6G. FIG. 6F shows the CFU per lung 12 h after infection. A single i.v. injection was given 1 h after the infection. FIG. 6G shows survival analysis of the mice which received 2 i.v. injections (1 h and 8 h after the infection). FIGS. 6H-L show the therapeutic efficiency of various treatments in a MRSA peritonitis mouse model. CFU in ascites, liver, kidneys, lung and spleen were determined 12 h after the infection. A single i.v. injection was given 1 h after the infection.

DETAILED DESCRIPTION

Figure 1:
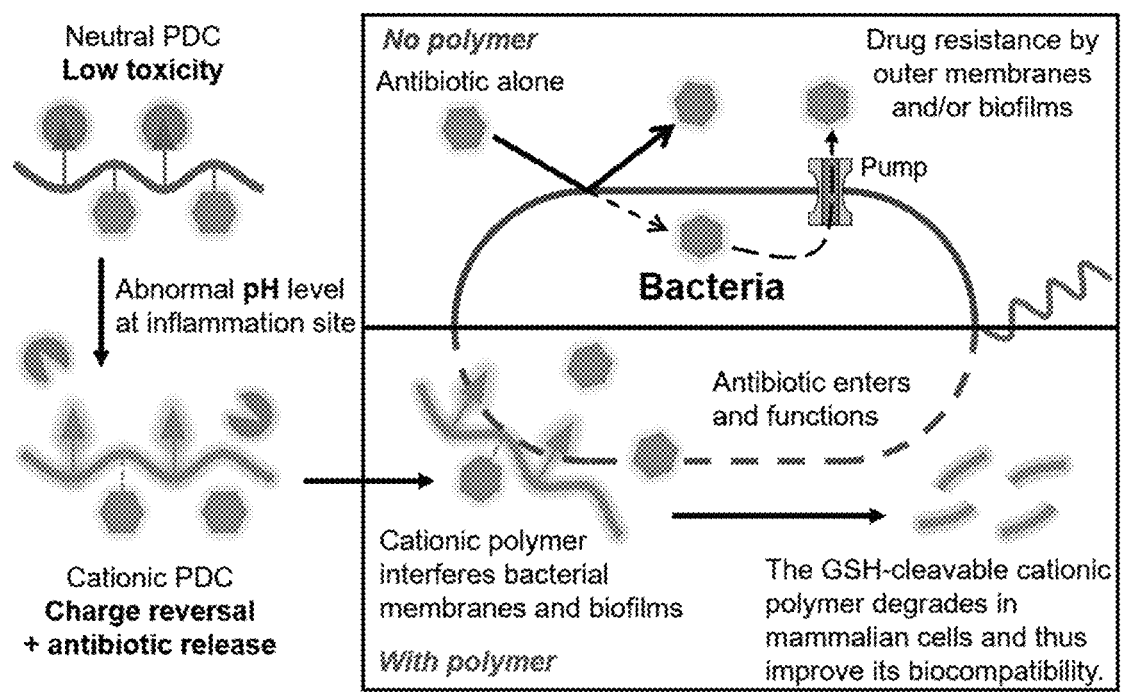
FIG. 1 shows a schematic illustration of a bio-degradable polymer-drug conjugate (PDC) of the present technology with low toxicity. In the acidic inflammatory microenvironment of infected tissue, the masked cationic groups of the PDC are revealed and the attached antibiotic is released due to pH-responsive elements. The two components (polymer and drug) in the PDC show synergistic effect in reducing minimum inhibitory concentration (MIC) of bacteria as well as lowering and even overcoming drug resistance.

The following terms are used throughout as defined below. All other terms and phrases used herein have their ordinary meanings as one of skill in the art would understand.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term—for example, "about 5 kD" would mean "5 kD±0.5 k D" or "4.5 kD to 5.5 kD."

"Conjugate" refers to two or more distinct molecular entities which are covalently linked to each other. Thus, a polymer-drug conjugate includes a polymer that is covalently linked to one or more drug molecules. A conjugate does not include non-covalent mixtures of molecular entities.

"Drug" as used herein refers to any suitable therapeutic agent. Drugs for use in the present technology are not particularly limited so long as they may be conjugated to a polymer of the present technology. The drug may be an antibiotic drug, or another type of drug.

"Effective amount" refers to the amount of compound (here, the PDC) or composition required to produce a desired effect. Hence, an effective amount of a compound or composition of the present technology in the context of treatment (i.e., "a therapeutically effective amount") refers to an amount of the compound or composition that alleviates, in whole or in part, symptoms associated with a disorder or disease, or slows or halts further progression or worsening of those symptoms. In the context of prevention, an effective amount prevents or provides prophylaxis for the disease or disorder in a subject at risk for developing the disease or disorder. One example of an effective amount includes amounts or dosages that yield acceptable toxicity and bioavailability levels for therapeutic (pharmaceutical) use including, but not limited to, the treatment of a bacterial infection, including infections by Gram-positive or Gram-negative bacteria. Determining a therapeutically effective amount of a compound described herein for treating a particular disorder or disease is well within the skill in the art in view of the present disclosure.

"Molecular weight" as used herein with respect to polymers refers to weight average molecular weights (Mw) and can be determined by techniques well known in the art including gel permeation chromatography (GPC). GPC analysis can be performed, for example, on a D6000M column calibrated with poly(methyl methacrylate) (PMMA) using triple detectors including a refractive index (RI) detector, a viscometer detector, and a light scattering detector, and dimethylformamide as the eluent.

Pharmaceutically acceptable salts of compounds described herein are within the scope of the present technology and include acid or base addition salts which retain the desired pharmacological activity and is not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydrobromic acid, nitric acid, sulfuric acid, and phosphoric acid), organic acids (e.g. alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g. $Na^+$, $Li^+$, $K^+$, $Ca^{2+}$, $Mg^{2+}$, $Zn^{2+}$), ammonia or organic amines (e.g. dicyclohexylamine, trimethylamine, triethylamine, pyridine, picoline, ethanolamine, diethanolamine, triethanolamine) or basic amino acids (e.g. arginine, lysine and ornithine). Such salts can be prepared in situ during isolation and purification of the compounds or by separately reacting the purified compound in its free base or free acid form with a suitable acid or base, respectively, and isolating the salt thus formed.

As used herein, a "subject" or "patient" is any animal subject to bacterial infections. In any embodiments, the subject is a mammal, such as a cat, dog, ungulate, rodent or primate. In any embodiments, the subject is a human. The term "subject" and "patient" can be used interchangeably.

"Treating" or "treatment" within the context of the present technology, means an alleviation, in whole or in part, of symptoms associated with a disorder or disease, or slowing, or halting of further progression or worsening of those symptoms. As a non-limiting example of treatment, a subject can be successfully treated for a bacterial infection if, after receiving through administration an effective or therapeutically effective amount of one or more PDCs or compositions described herein, the subject shows observable and/or measurable reduction in or absence of one or more signs and symptoms of the infection such as, but not limited to, reduction or elimination of bacterial load, fever, headache, nausea, vomiting, runny nose, and cough, increased energy, or improvement in quality of life relating thereto. Treatment, as defined herein, of a subject, including a human being, is subject to medical aid with the object of improving the subject's condition, directly or indirectly. Treatment typically refers to the administration of an effective amount of a PDC or PDC composition as described herein.

In one aspect, the present technology provides a polymer-drug conjugate that includes a polymer comprising a plurality of masked cationic functional groups wherein the masked cationic functional groups are converted in aqueous solution to free cationic functional groups faster at a pH below 7 than a pH above 7 (or in some embodiments, a pH at or above 7); wherein the cationic functional groups at each occurrence are independently masked as either an uncharged functional group or by an ion pair with a neighboring anionic functional group attached to the polymer. The PDC also includes an antibiotic drug linked to the polymer by a pH-sensitive linker that releases the drug faster in aqueous solution at or below a pre-determined pH value selected from a range of 4.5 to 7 than a pH value above 7.

In any embodiments of the polymer-drug conjugate, one or more of the plurality of masked cationic functional groups may be present in a backbone of the polymer, in one or more side-chains of the polymer, or in both the backbone and one or more side-chains of the polymer. In any embodiments, the one or more of the plurality of masked cationic functional groups of the polymer may be present in one or more side-chains of the polymer.

In any embodiments of the polymer-drug conjugate, the plurality of masked cationic functional groups comprise amide, amine and/or ammonium functional groups. For example, the masked cationic functional group may be an amide that at certain pH values (e.g., values below 7) may release the amine group, which becomes protonated under such conditions. In some embodiments, the pH value may be 4.5, 5, 5.5, 6, 6.5, 6.7, <7 or a range between any two of the foregoing values. The masked cationic functional group may also be an ammonium group that is ion paired ("neutralized") with a neighboring anionic functional group attached to the polymer.

The neighboring anionic functional group attached to the polymer may be a carboxyl or carboxylate group. In any embodiments, the masked cationic functional group may be an ammonium group and the neighboring anionic functional group may be a carboxylate. It will be understood that under some circumstances, one of the ammonium/carboxylate ion pair may also be present in their non-ionized forms, including, e.g., under non-physiological conditions with a pH well below or well above the pKas of either group. In any embodiments, the plurality of masked cationic functional groups may include both amide groups and ammonium groups, neutralized by neighboring carboxylate groups attached to the polymer. In any embodiments, the anionic functional group may be a 2,3-dimethylmaleic acid or a cis-aconitic acid attached to the polymer through an amide group.

In any embodiments, the polymer-drug conjugate may include a polymer selected from the group consisting of polyurea, polyurethane, polypeptide, poly(β-amino ester), polyester and combinations thereof. In any embodiments the polymer may be a polyurea. The polymer may also be branched or unbranched (i.e., linear); in any embodiments it may be a copolymer such as a block copolymer, a graft copolymer, or a random copolymer. In any embodiments the polymer may be linear, such as a linear polyurea or a linear polyurethane. In any embodiments, the polymer may include one or more disulfide bonds in a backbone of the polymer. In any embodiments the polymer may comprise a cystine group. Polymers suitable for use in the present polymer-drug conjugates may be any suitable size that allows the polymer to interact with microbial cell membranes such as bacterial cell membranes. In any embodiments, the polymer may have a weight average molecular weight of about 1 kD to about 40 kD, including, without limitation, about 1 kD, about 2 kD, about 3 kD, about 4 kD, about 5 kD, about 6 kD, about 7 kD, about 8 kD, about 9 kD, about 10 kD, about 15 kD, about 20 kD, about 25 kD, about 30 kD, about 35 kD, about 40 kD, or a range between and including any two of the foregoing values. For example, the polymer may have a weight average molecular weight of about 1 kD to about 0 kD, about 2 kD to about 20 kD, or about 6 kD to about 8 kD. In any embodiments, the polymer may have a weight average molecular weight of about 7 kD.

In any embodiments, the polymer may include repeating subunits having an unbranched $C_{2-12}$ alkylene chain. In any embodiments, the polymer may include repeating subunits having an unbranched $C_{4-10}$ or $C_{4-8}$ or $C_6$ alkylene chain. In some embodiments the polymer may be a polyurea comprising repeating subunits comprising an unbranched $C_{2-12}$ alkylene chain and comprising disulfide bonds. The polymer-drug conjugate may include repeating subunits that comprise one or more cystine groups. Optionally, the cystine group may further include masked cationic functional groups. For example, in any embodiments, the masked cationic functional group may include diethyltriamine attached to 2,3-dimethyl maleic acid or cis-aconitic acid via an amide bond. Optionally, the cystine group may include one or two antibiotic drugs attached to the cystine by pH-sensitive linkers as described herein. Where two antibiotic drugs are attached, it will be understood that other repeating subunits will include the masked cationic functional groups.

In any embodiments of the polymer-drug conjugate herein, the polymer may include one or more subunits of one or more of the following structures, wherein one or both of n and p are independently an integer of 1-70, and q is 0-70 provided n+p+q=2-70, R is H or —C(O)C(CH$_3$)═C(CH$_3$)C(O)OH, and the Drug is any antibiotic drug as described herein.

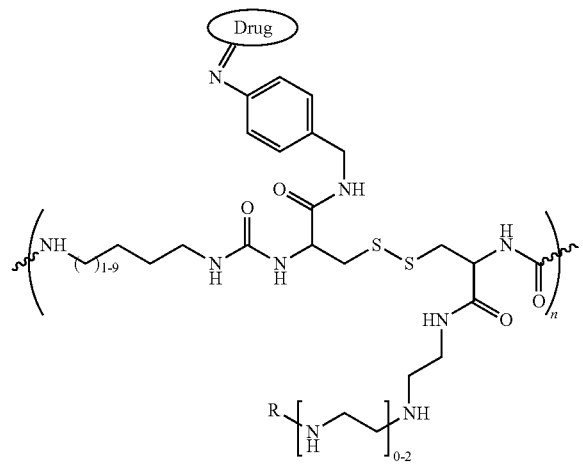

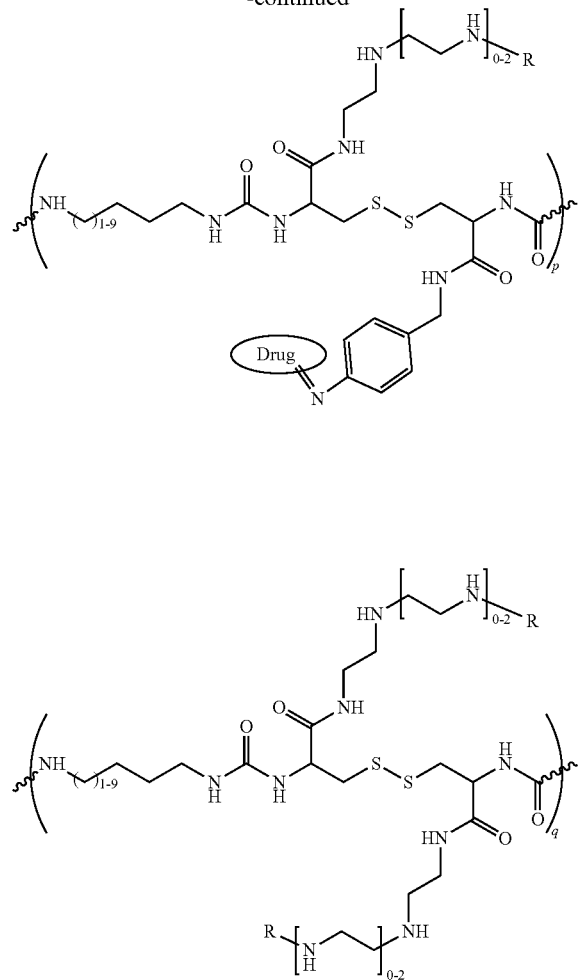

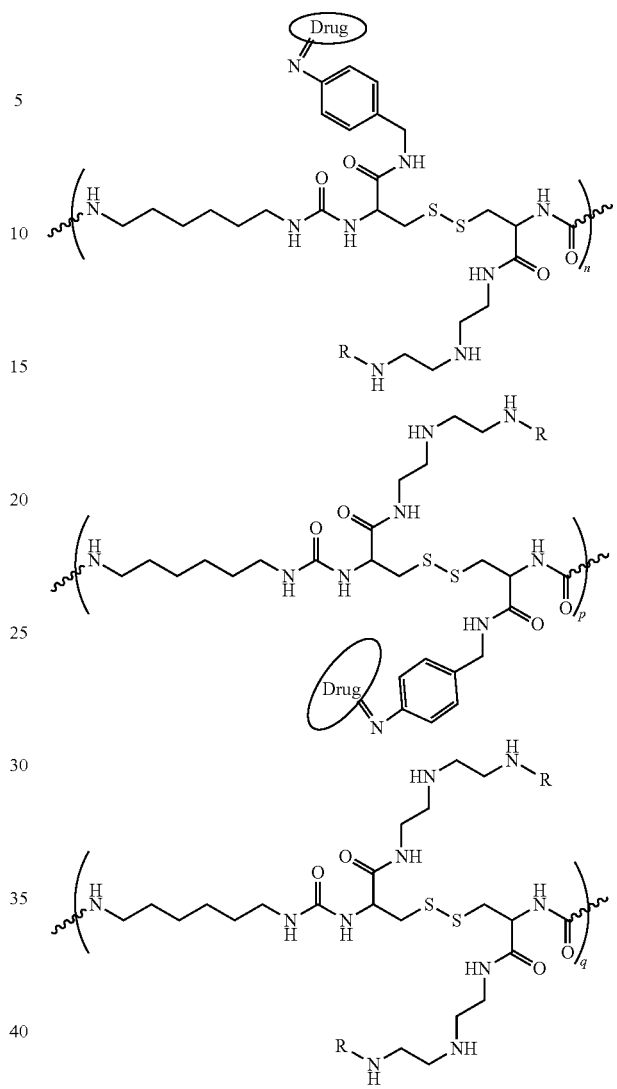

It will be appreciated that the alkyl segment in the polyurea backbone of the subunits above may have from 4-12 carbons as indicated, including 4, 5, 6, 7, 8, 9, 10, 11, or 12 carbons or a range encompassing any two of the foregoing values, e.g., 4-8 carbons, or, in any embodiments, 6 carbons. It will further be appreciated that the cationic side chains may be of variable length as shown with 1, 2, or 3 ethylene amino groups (corresponding to 0, 1, and 2 of the optional groups). In any embodiments, there are 2 ethylene amino groups. In any embodiments, n+p+q=2-40 or 4-20. In any embodiments, the polymer may have a polydispersity (e.g., PDI=Mw/Mn and measured e.g., using gel permeation) of from 1 to 2 or greater than 1 to 2). In any embodiments the PDI may be 1, 1.1, 1.2, 1.3, 1.4, 1.5, 1.6, 1.7, 1.8, 1.9, 2 or a range between and including any two of the foregoing values (e.g., 1.1 to 1.9). It will be understood that the subunits need not be consecutively attached to each other in a particular order. Depending on whether a homogenous or heterogenous mixture of subunits are used and how the polymerization is carried out, the subunits may be polymerized to form a random copolymer or block copolymer.

Thus in any embodiments, the subunits may comprise one, two, or all three of the following structures:

Further, in any embodiments, the subunit may be in its unmasked form in which the 2,3-dimethylmaleic acid group is not present, and the cationic polymer may contain a mixture of masked and unmasked amino/ammonium groups, or the cationic polymer may be completely unmasked without any 2,3-dimethylmaleic acid groups present. In any embodiments, one or more of the subunits may contain a 4-aminobenzylamine group without an imine linkage to the antibiotic.

A variety of antibiotics may be used in the polymer-drug conjugate of the present technology so long as they have both sufficient water solubility and potency so that when released in infected tissue, the antibiotic reaches therapeutically effective concentrations. In any embodiments, the antibiotic may be one or more of streptomycin, clindamycin, gentamycin, ciprofloxacin, vancomycin, sulfathiazole, spectinomycin, roxithromycin, sisomicin, novobiocin, isoniazide, rifampicin, clarithromycin, salinomycin and roxithromycin. In any embodiments, the antibiotic is streptomycin. In any embodiments, the antibiotic may be conjugated to the polymer through a pH-sensitive linker selected from the group consisting of hydrazone, 2,3-dimethyl maleic acid ester and/or amide, imine, ketal, acetal and phenyl boronic acid or ester. In any embodiments, the linker is an imine.

In some embodiments, the present technology provides a PDC including a polyurea having a weight average molecular weight from 6 kD to 8 kD and an antibiotic drug linked to the polyurea by a pH-sensitive linker. The polyurea bears a plurality of masked and/or unmasked cationic functional groups selected from amide, amine, and ammonium functional groups in one or more side chains of the polyurea. The cationic functional groups are masked as either an uncharged functional group (e.g., amine or amide) or by an ion pair with a neighboring carboxyl or carboxylate attached to the polymer, e.g., in the same side chain(s) containing the cationic functional groups. The polyurea may further include a disulfide linkage in some or all of the repeating subunits making up the polyurea; i.e., the polyurea backbone includes disulfide linkages. The pH-sensitive linker may be attached to the polymer as a 2,3-dimethylmaleic acid or cis-aconitic acid through an amide group.

In another aspect the present technology provides an unmasked polymer-drug conjugate which includes a polymer comprising a plurality of cationic functional groups; and an antibiotic drug linked to the cationic polymer by a pH-sensitive linker that releases the drug faster in aqueous solution at or below a pre-determined pH value selected from a range of 4.5 to 7 than a pH value above 7. Such an unmasked polymer-drug conjugate may include any of the features of the masked polymer-drug conjugate other than the masking groups.

Figure 2:
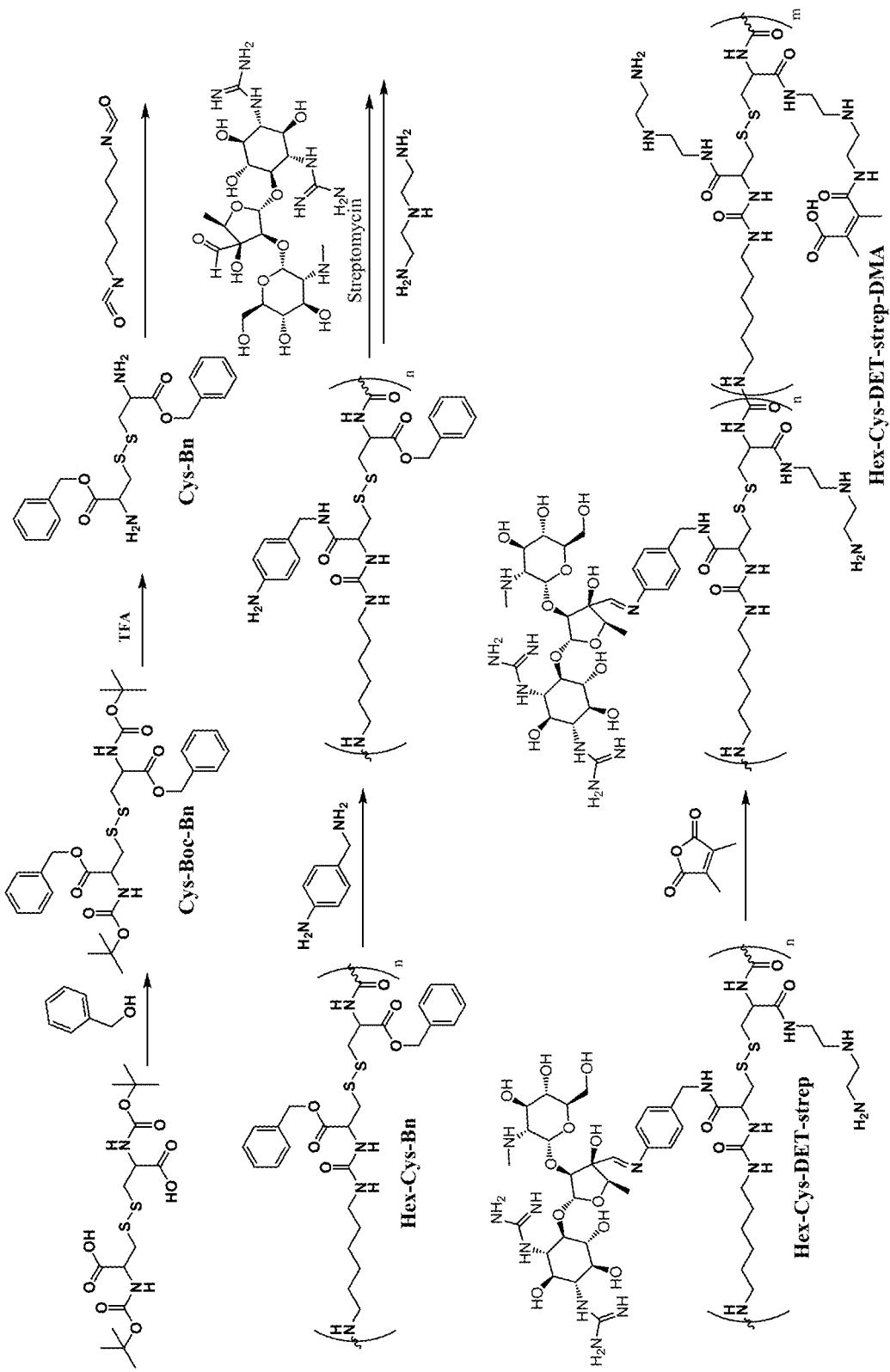
FIG. 2 shows a synthetic scheme for preparing one embodiment of a PDC of the present technology.

The polymer-drug conjugates described herein may be prepared by polymerization and coupling methods known in the art. In some embodiments a disulfide compound that contains one or more (e.g., 2 or 3) amine or hydroxyl groups may be reacted with a diisocyanate under standard conditions to form polyurea or polyurethane polymers. In any embodiments, the disulfide compound comprises two amino groups, and may be, e.g., cystine. The diisocyanates may include an alkylene chain having 4 to 12 carbons, e.g. 6 carbons. The disulfide compounds also bear carboxyl groups or other groups to which masked cationic groups may be added or the masked cationic groups may themselves be present as protected groups. For example polyamines having 2, 3, or 4 amine groups may be attached via an amide bond to such carboxyl groups using standard peptide coupling techniques. In some embodiments the polyamine is diethylenetriamine. Other functionalized amines that allow for the attachment of the antibiotic to the polymer via a pH-sensitive linker may be attached to the polymer at carboxyl or other suitable groups on the polymer. For example, 4-aminobenzylamine may be used to form a 4-amino-N-benzylamide, where the 4-amino may later be functionalized as an imine by reaction with an antibiotic having an aldehyde. Other pH-sensitive linkers may be used to attach the antibiotic, including hydrazone, 2,3-dimethyl maleic acid ester and/or amide, imine, ketal, acetal and phenyl boronic acid or ester. It will be appreciated that those of skill in the art will know how to select a suitable pH-sensitive linker group for the desired polymer-drug conjugate in view of the present disclosure. FIG. 2 schematically shows preparation of an illustrative embodiment of the present technology, and may be readily modified by those of skill in the art to prepare additional variations as described above.

While not wishing to be bound by theory, the efficacy of the disclosed polymer-drug conjugates in treating bacterial infection (including drug-resistant infections) is believed to rest on several features, as shown in FIG. 1. Drug-resistant bacteria often rely on barring antibiotics from crossing the bacterial cell wall/membrane and/or pumping them back outside into the extracellular environment if they do get in. The present pH-responsive PDC can counteract these bacterial strategies. The polymer of the PDC carries latent (masked) positive charges to minimize toxicity to healthy tissue. Upon entering the lower pH environment of infected tissue, the pH-sensitive masking groups of the PDC are released, revealing the positive charges of the polymer. In its unmasked cationic form, the polymer's strong positive charge facilitates interactions of the PDC with the negatively charged bacterial surface, inducing pores on the bacterial wall/membrane and damaging the bacteria. At the same time, the low pH of the infected tissue causes the pH-sensitive linker to degrade, releasing the antibiotic at the surface of the disrupted membrane. The antibiotic cannot be excluded and is able to cross the bacterial cell membrane. If it is pumped out, the antibiotic is able to diffuse back into the bacterial cell due to the disrupted membrane. This antibacterial effect of the PDC is amplified because the positively charged PDC binds to the bacteria's surface and acts as a drug reservoir to release drugs locally. The strong synergistic effect between the cationic polymer and antibiotic of the PDC can diminish the drug resistance of pathogens, leading to significantly enhanced antibacterial efficacy while minimizing the required PDC dosage. The PDC is also more biocompatible than normal cationic polymers. When the polymer encounters a reducing environment, such as the interior of a mammalian cell with glutathione, the disulfide bonds of the polymer are cleaved, degrading the polymer into smaller subunits, which have less toxicity.

The present technology provides pharmaceutical compositions and medicaments comprising any one of the embodiments of the polymer-drug conjugates disclosed herein and one or more pharmaceutically acceptable carriers or excipients. The compositions may be used in the methods and treatments described herein. The pharmaceutical composition may include an effective amount of any of one of the embodiments of the compositions disclosed herein for treating a bacterial infection in a subject.

The compositions described herein can be formulated for various routes of administration, for example, by parenteral, rectal, nasal, vaginal administration, or via implanted reservoir. Parenteral or systemic administration includes, but is not limited to, subcutaneous, intravenous, intraperitoneal, and intramuscular injections. The following dosage forms are given by way of example and should not be construed as limiting the instant present technology.

Injectable dosage forms generally include solutions or aqueous suspensions which may be prepared using a suitable dispersant or wetting agent and a suspending agent so long as such agents do not interfere with formation of the PDCs described herein. Injectable forms may be prepared with acceptable solvents or vehicles including, but not limited to sterilized water, Ringer's solution, 5% dextrose, or an isotonic aqueous saline solution.

Besides those representative dosage forms described above, pharmaceutically acceptable excipients and carriers are generally known to those skilled in the art and are thus included in the instant present technology. Such excipients and carriers are described, for example, in "Remingtons Pharmaceutical Sciences" Mack Pub. Co., New Jersey (1991), which is incorporated herein by reference. Thus, the present technology provides a pharmaceutical composition comprising any polymer-drug conjugate as described herein and a pharmaceutically acceptable carrier or excipient.

Specific dosages may be adjusted depending on conditions of disease, the age, body weight, general health conditions, sex, and diet of the subject, dose intervals, administration routes, excretion rate, and combinations of polymer-drug conjugates. Any of the above dosage forms containing effective amounts are well within the bounds of routine experimentation and therefore, well within the scope of the instant present technology. By way of example only, such dosages may be used to administer effective amounts of the cationic peptide drug(s) to the patient and may include about 0.1 mg/kg, about 0.2 mg/kg, about 0.3 mg/kg, about 0.4 mg/kg, about 0.5 mg/kg, about 0.75 mg/kg, about 1 mg/kg, about 1.25 mg/kg, about 1.5 mg/kg, or a range between and including any two of the forgoing values. Such amounts may be administered parenterally as described herein and may take place over a period of time including but not limited to 5 minutes, 10 minutes, 20 minutes, 30 minutes, 45 minutes, 1 hour, 2 hours, 3 hours, 5 hours, 10 hours, 12, hours, 15 hours, 20 hours, 24 hours or a range between and including any of the foregoing values. The frequency of administration may vary, for example, once or twice per day, per 2 days, per 3 days, per week, per 10 days, per 2 weeks, or a range between and including any of the foregoing frequencies. Alternatively, the compositions may be administered once per day on 2, 3, 4, 5, 6 or 7 consecutive days. A complete regimen may thus be completed in only a few days or over the course of 1, 2, 3, 4 or more weeks.

In one aspect, the present polymer-drug conjugates are useful for the treatment of bacterial infections. The methods include administering to a subject suffering from a bacterial infection an effective amount of any PDC described herein. In any embodiment of the methods, the subject is infected by a drug-resistant bacterial strain and/or a bacterial biofilm. Both Gram-negative and Gram-positive bacterial infections may be treated, depending on the nature of the antibiotic incorporated into the PDC. For example, in any embodiments, the subject may be infected with one or more of enterococcal or staphylococcal bacteria. In any embodiments, the subject may be infected with *Pseudomonas* bacteria. In any embodiments, the subject may be infected with one or more of *E. coli, S. aureus* (including methicillin-resistant *S. aureus*, known as MRSA), and *P. aeruginosa*.

The examples herein are provided to illustrate advantages of the present technology and to further assist a person of ordinary skill in the art with preparing or using the polymer-drug conjugates of the present technology. To the extent that the compositions include ionizable components, salts such as pharmaceutically acceptable salts of such components may also be used. The examples herein are also presented in order to more fully illustrate certain aspects of the present technology. The examples should in no way be construed as limiting the scope of the present technology, as defined by the appended claims. The examples can include or incorporate any of the variations, aspects or aspects of the present technology described above. The variations, aspects or aspects described above may also further each include or incorporate the variations of any or all other variations, aspects or aspects of the present technology.

EXAMPLES

Materials. N,N'-Di-Boc-L-cystine, streptomycin sulfate, N,N'-dicyclohexylcarbodiimide (DCC) and 2,3-dimethylmaleic anhydride (DMA) were purchased from Chem-Impex/Int'l., Inc. (Wood Dale, Ill., USA). 1,6-Diisocyanatohexane, and 4-aminobenzylamine were purchased from Acros Organics (Pittsburgh, Pa., USA). Hydroxybenzotriazole (HoBt) was purchased from Abovchem (San Diego, Calif., USA). Diethylenetriamine was purchased from Alfa Aesar (Tewksbury, Mass., USA). Other reagents were purchased from Thermo Fisher Scientific (Fitchburg, Wis., USA) and used as received unless otherwise stated.

Characterization. $^1$H NMR spectra of all intermediate and final polymer products were recorded on a Bruker 400 spectrometer in $CDCl_3$ at 25° C. The molecular weights (Mn and Mw) and polydispersity indices (PDI) of the polymers were determined by a gel permeation chromatographer (GPC) equipped with a refractive index detector, a light scattering detector, and a viscometer detector (Viscotek, USA). DMF with 10 mmol/L of LiBr was used as the mobile phase with a flow rate of 1 mL/min.

Example 1—Preparation of a Polymer-Drug Conjugate of the Present Technology

FIG. 2 shows a synthetic scheme for preparation of a polymer-drug conjugate according to the present technology and described in more detail below.

Synthesis of the N,N'-Di-Boc-L-cystine benzyl ester ($Boc_2$-Cys-Cys-$Bn_2$). N,N'-Di-Boc-L-cystine (10 g, 22.7 mmol), benzyl alcohol (8.34 g, 77.2 mmol) and HoBt (6.13 g, 45.4 mmol) were dissolved in 200 mL anhydrous THF and cooled to 0° C. in the ice bath. Dicyclohexylcarbodiimide (DCC, 11.2 g, 54.4 mmol) was dissolved in 100 mL tetrahydrofuran (THF) and added dropwise into the above solution. The mixture was stirred at room temperature for 12 h and filtered to remove dicyclohexylurea. The filtrate was concentrated by rotary evaporation and purified by column chromatography (Hex:EtAc=4:1). The product was obtained as a white powder (yield 91%). $^1$H NMR in $CDCl_3$, δppm: 7.3 (s, 10H), 5.1 (s, 4H), 4.6 (s, 2H), 3.1 (s, 4H), 1.3 (s, 18H).

Synthesis of the Hex-Cys-Cys-$Bn_2$ polymer. $Boc_2$-Cys-Cys-$Bn_2$ (1 g, 1.61 mmol) was dissolved in 10 mL dichloromethane (DCM) and added with 10 mL trifluoroacetic acid (TFA) for deprotection. After stirring at room temperature for 2 h, the mixture was dried by rotary evaporation and followed by a further vacuum to completely remove the free TFA. The resultant product, together with 1,6-Diisocyanatohexane (0.27 g, 1.61 mmol) and triethylamine (TEA, 666 L), was dissolved in 4 mL anhydrous dimethyl formamide (DMF) and polymerized at 70° C. for 3 h, under $N_2$ protection. The product Hex-Cys-Cys-$Bn_2$ polymer was reprecipitated in diethyl ether for three times and dried under vacuum, yielding white powders (95%). $^1$H NMR in DMSO-d6, δppm: 7.3 (10H), 6.4 (2H), 6.2 (2H), 5.1 (4H), 4.5 (2H), 3.1 (4H), 2.8 (4H), 1.1-1.4 (8H).

Synthesis of the Hex-Cys-Cys-$DET_2$ polymer. Hex-Cys-Cys-$Bn_2$ polymer (0.2 g) was dissolved in 1.5 mL DMF, and was slowly added into 2 mL diethylenetriamine (DET, 0.72 mL, 6.6 mmol) in DMF solution at 0° C. The reaction was stirred at 0° C. for 1 h and then warmed to room temperature for another 2 h. The product was obtained by reprecipitating in diethyl ether for four times and dried under vacuum (yield 94%). $^1$H NMR in $D_2O$, δppm: 4.2-4.4 (2H), 3.3 (4H), 3.0 (4H), 2.8 (4H), 2.6-2.8 (12H), 1.4 (4H), 1.2 (4H).

Synthesis of the polymer-drug conjugate Hex-Cys-Cys-DET-strep. Hex-Cys-Cys-$Bn_2$ polymer (0.2 g) was dissolved in 1.5 mL DMF, followed by adding 0.1 mL 4-aminobenzylamine (8.1 mg, 66 μmol) in DMF solution under 0° C. The mixture was stirred at 0° C. for 2 h, reprecipitated in diethyl ether for three times, dried under vacuum and then redissolved in 1.5 mL Dimethylsulfoxide (DMSO). Streptomycin sulfate (36 mg, 50 μmol) and TEA (20 μL, 144 μmol) were dissolved in 2 mL formamide and added into the above solution. The mixture was stirred at 40° C. for 12 h, then cooled to 0° C. and slowly added into 2 mL diethylenetriamine (DET, 0.72 mL, 6.6 mmol) in DMF solution.

The reaction was stirred at 0° C. for 2 h and then the final product was obtained by reprecipitating in diethyl ether for four times and dried under vacuum (yield 90%). Hex-Cys-Cys-DET-strep: $^1$H NMR in D$_2$O, δppm: 7.7 (0.15H), 7.0 (0.36H), 6.7 (0.36H), 5.0-5.4 (0.68H), 4.2-4.4 (2.35H), 3.4-3.8 (4H), 3.2-3.4 (3.7H), 2.9-3.2 (4H), 2.5-2.9 (11.1H), 2.5-3.9 (2.25H), 1.4 (4H), 1.2 (4H), 1.1 (0.46H).

Synthesis of the neutralized Hex-Cys-Cys-DET-DMA polymer. Hex-Cys-Cys-DET$_2$ polymer (0.15 g) and DMA (28 mg, 227 µmol) and TEA (35 µL, 250 µmol) were dissolved in 3 mL anhydrous DMSO and stirred at room temperature overnight. The neutralized product Hex-Cys-Cys-DET-DMA was obtained by reprecipitating in acetone/ethyl ether for four times and dried under vacuum (yield 93%). The neutralized polymer-drug conjugate Hex-Cys-DET-Strep-DMA was synthesized following the same procedure.

Hex-Cys-Cys-DET-DMA (polymer without drug): $^1$H NMR in D$_2$O, δppm: 4.1-4.6 (2H), 3.7 (4H), 3.5 (4H), 3.2 (4H), 2.7-3.3 (12H), 1.7-1.9 (6.22H), 1.4 (4H), 1.2 (4H).

Hex-Cys-Cys-DET-strep-DMA: $^1$H NMR in D$_2$O, δppm: 7.7 (0.14H), 7.0 (0.36H), 6.7 (0.36H), 5.0-5.4 (0.67H), 4.2-4.5 (2.30H), 3.4-3.8 (4H), 3.2-3.4 (3.7H), 2.9-3.2 (4H), 2.5-2.9 (11.1H), 2.5-3.9 (2.25H), 1.7 (6.36H), 1.4 (4H), 1.2 (4H), 1.1 (0.46H).

According to the $^1$H NMR of Hex-Cys-Cys-DET-strep-DMA, each repeat unit of the polymer conjugates 0.145 streptomycin and 1.06 DMA on average, leading to a loading content of 10.2%. A loading efficiency of 97.5% was determined by comparing the actual loading content and the theoretic loading content calculated by the polymer and antibiotic feed ratio. The weight average molecular weight of the Hex-Cys-Bn polymer was 7.1 kD; the number average molecular weight was 5.5 kD; and the polydispersity (PDI) was therefore 1.3, all as measured by gel permeation chromatography (GPC). The antibiotic release rates under different pH values may be adjusted through variation in the pH sensitive linker. Drug release profiles were measured using HPLC and showed that the PDC was quite stable at pH 7.4, with about 20% of streptomycin release at 48 h. The antibiotic release was significantly accelerated at lower pH at pH 6.0, about 70% streptomycin was released within 48 h (FIG. 3A).

Example 2—Biological Methods

Bacterial strains. S. aureus Newman was kindly provided by Prof Douglas Weibel; E. coli ATCC25922, S. aureus ATCC 33591 and P. aeruginosa ATCC 27853 were kindly donated by Prof. David Andes. E. coli DH5a was purchased from Thermo Fisher. The bacteria above were grown in Mueller Hinton Broth (MHB) media (Criterion, Santa Maria, Calif., USA). M. smegmatis mc$^2$155 strain was kindly donated by Prof. Adel M. Talaat, and was grown in Middlebrook 7H9 broth (HiMedia, West Chester, Pa., USA).

Minimal inhibitory concentration (MIC) measurements. The MIC of the different treatments on various bacteria strains was determined using the broth microdilution method. Briefly, 100 µL of the respective broth media containing serial twofold dilutions of each compound was placed into a 96-well tissue culture plate. Each bacterial strain was taken from an exponentially growing culture and diluted to 5×10$^6$ CFU/mL. 10 µL of such microbial suspension was inoculated in each well of the plate, resulting in a final bacteria concentration of approximately 5×10$^5$ CFU/mL. The bacteria were cultured at 37° C. for 24 h and their growth were observed by reading the optical density (OD) at 600 nm. The MIC was determined as the treatment concentration at which no microbial growth was observed. Broth containing microbial cells alone was used as a positive control and broth without bacteria inoculation was used as a negative control. Each test was carried out in 3 replicates.

Fractional inhibitory concentration (FIC) measurement. The synergy between the cationic polymer and streptomycin was assessed by checkerboard assays. The two antibacterial components were mixed in a 96-well plate with serial two-dimensional dilutions. Bacteria were inoculated in each well of the plate and their growth, reflected by the OD600 value, were monitored. The synergy effect was evaluated by calculating the FIC index according to the formula below:

$$FIC = \frac{MIC_A^{Comb}}{MIC_A} + \frac{MIC_B^{Comb}}{MIC_B}$$

$MIC_A^{Comb}$ and $MIC_B^{Comb}$ indicate the MICs of the two components in combination. The interactions between the two components are defined according to standard criteria of considering FIC≤0.5 as synergistic; 0.5<FIC≤1 as additive; 1<FIC≤4 as indifference; and FIC>4 as antagonism.

Cell viability test. Cytotoxicity of different components was tested through MTT assays. HEK 293 human embryonic kidney cells were seeded onto a 96-well plate (1×10$^4$ cells/well) and cultured overnight. The cells were then treated with various polymers or PDCs with serial dilutions for 48 h and their viability was measured by a standard MTT assay. Data were collected by monitoring the difference between the absorbance at 560 nm and 650 nm using a GloMax-Multi Microplate Multimode Reader (Promega, Wis., USA).

Hemolysis assay. The fresh human blood sample was purchased from BioIVT elevating science and the blood cell was collected through a centrifuge at 5000 rpm for 5 min, washed with PBS buffer for 3 times and suspended in PBS to a final concentration of approximately 4% (v/v). The antibacterial polymer and PDC with different charges were serial diluted with PBS and placed in 96-well plates (100 µL/well). The blood cell suspension (10 µL/well) was added into the wells and incubated at 37° C. for 1 h to allow the complete hemolysis process. PBS and Milli-Q water containing 1% Triton X-100 were acting as negative and positive controls, respectively. Following centrifugation at 3000 rpm for 7 min, the supernatant (70 µL/well) was transferred to another clean 96-well plate. OD 560 in each well was monitored by a microplate reader, and hemolysis was calculated using the following formula:

$$\text{Hemolysis (\%)} = \frac{OD\ 560_{Sample} - OD\ 560_{PBS}}{OD\ 560_{Triton} - OD\ 560_{PBS}} \times 100\%$$

Streptomycin release kinetics. The PDC was dissolved in PBS solution with different pH values (30 mg/mL, pH 6.0, 6.5, 7.0) and sealed in dialysis bags (MWCO 3500). The bags were put into the PBS buffers with the corresponding pH, and incubated in a 37° C. shaker. At different time intervals, 100 µL sample outside the dialysis bag was collected for HPLC analysis.

Live/Dead bacterial staining assay. Exponentially growing bacteria (E. coli ATCC 25922) were collected by centrifugation at 8000 rpm for 5 min, washed with saline and diluted to OD 600 value of 0.5. The bacterial suspensions were incubated with different treatments at 37° C. for 0.5 h and 3 h, and then washed with saline and stained by acridine orange (10 μg/mL) and ethidium bromide (EB, 10 g/mL) solution for 15 min. Afterward, the bacteria were collected via centrifugation, washed with saline for 2 times, resuspended in 70% glycerol and spread on glass slides. The live/dead bacteria were observed by a confocal laser scanning microscope (CLSM).

PDC and bacteria colocalization assay. Exponentially growing bacteria (E. coli ATCC 25922, MRSA ATCC 33591 and P. aeruginosa ATCC 27853) were collected by centrifugation at 8000 rpm for 5 min, washed with saline and diluted to OD 600 value of 0.5. The bacteria suspensions were stained by acridine orange (10 μg/mL) solution for 15 min, and then incubated with Cy5 tagged PDC (500 μg/mL) solution at different pH for 10 min or 60 min. After washed with saline for two times, the bacteria were resuspended in 70% glycerol and observed by CLSM.

Scanning electron microscopy (SEM) observation. Bacteria suspensions were prepared as above and treated with PDC at different pH for 3 h, washed with saline and fixed with 2.5% glutaraldehyde at 4° C. overnight. The samples were washed with Milli-Q water and dehydrated with a series of graded ethanol solutions (50%, 75%, 90%, 100%, each for 5 min). After drying for 1 day, the samples were coated with platinum and observed by SEM (Zeiss/LEO 1530).

Biofilm inhibition assays. Exponentially growing bacteria were inoculated into 96 well plates ($1\times10^4$ cell/well) containing MHB broth with 2% (v/w) glucose, incubated under stationary conditions at 37° C. for one day. After biofilm formation, the media was discarded and the plates were washed with PBS to remove the planktonic bacteria. Fresh NMB broth containing serially diluted free streptomycin or PDC were added to the plates and incubated at 37° C. for another 24 h. The media in each well was then removed, and the plates were washed carefully with PBS for 1 time. The biofilm in each well was fixed with 95% ethanol for 15 min and stained with 0.1% crystal violet for 15 min. After washing with Milli-Q water for three times, 33% v/v acetic acid (100 μL/well) was added to solubilize the crystal violet staining. OD 560 in each well was read to determine the biofilm formation. The biofilm formed as described above was also stained with acridine orange and Cy5 labeled PDC, and monitored by CLSM to observe the PDC penetration.

Evaluation of antibiotic resistance development. E. coli ATCC 25922 was employed to study the drug resistance development under sublethal dose treatments of free streptomycin, cationic polymer or the PDC. During a serial of passages, the MIC of each treatment was measured by the broth microdilution method as described above, and the bacteria were exposed to ½MIC at that particular passage. MIC for each passage was recorded and normalized to that of the first passage to determine the drug resistance enhancement.

Antibacterial activity for intracellular infection. The antibacterial activity for intracellular infection was tested following the previous report. Briefly, macrophage Raw 264.7 cells were seeded in 96-well plate at a density of $1\times10^4$ cell/swell overnight and infected with MRSA or P. aeruginosa at a ratio of 10-20 bacteria per macrophage in FBS free RPMI 1640 medium. After 3 h incubation, the cells were washed and cultured in 1640 medium containing 10% FBS and 50 μg/mL gentamycin for one day to prevent the growth of extracellular bacteria. Then the macrophages were treated with free streptomycin or PDC for another day and lysed with Milli-Q water supplemented with 0.1% Triton-X. The cell lysates were serially diluted and the CFU in each well was determined by plating on MHB agar plates.

In vivo imaging of MRSA infection. The targeting ability of the PDC to MRSA infection site was investigated through in vivo imaging. The lower body of the ICR mice (female, 22-24 g, Charles River, n=3) were shaved and the right thigh was infected with MRSA ($5\times10^6$ CFU/mouse) one day before imaging. Cy5 labeled PDC was given through i.v. injection and the fluorescence images were captured through an IVIS system at scheduled time points (0, 0.5, 1, 2, 4, 8, 24 h post-injection). For ex vivo imaging, the mice were sacrificed at 24 h after injection and the major organs including heart, kidneys, spleen, lung, liver and both thighs were excised, washed with 0.9% saline and imaged.

Mouse thigh infection model. ICR mice (female, 22-24 g, Charles River) were intramuscularly inoculated with E. coli ATCC 25922 ($2\times10^8$ CFU/mL in saline, 0.05 mL bacteria suspension per thigh) on their both thighs and randomly divided into 4 groups (n=3). The mice were treated with PBS, free streptomycin (5 mg/kg), polymer alone (50 mg/kg, streptomycin equivalent of 5 mg/kg) or PDC (50 mg/kg) through i.v. injection 1 h after the infection. 24 h after the inoculation, animals were euthanized by $CO_2$ asphyxiation and thigh muscles were collected and homogenized in 5 mL cold PBS with glass homogenizer. The homogenates in the amount of 0.1 mL were used for serial tenfold dilutions and spread onto nutrient agar plate for CFU determination.

Mouse lung infection model. ICR mice (female, 22-24 g, Charles River) were immunosuppressed with two intraperitoneal (i. p.) injections of cyclophosphamide at 4 days (150 mg/kg) and 1 day (100 mg/kg) before infection. At day 0, P. aeruginosa ATCC 27853 ($1\times10^8$ CFU/mL in saline, 0.05 mL bacteria suspension per injection) was inoculated into the lungs through intratracheal injection under isoflurane anesthesia, and the infected mice were randomly divided into 4 groups (n=5). 1 h after the infection, a single dose of different treatments was given through i.v. injection. 12 h after the inoculation, the animals were euthanized by $CO_2$ asphyxiation and their lungs were harvested and homogenized in 5 mL cold PBS for CFU determination. In another experiment of monitoring the mice survival for the lung infection model, the P. aeruginosa infected mice were given 2 treatments (1 h and 8 h after the infection) and their survival was observed using Kaplan-Meier curves (n=5).

Mouse peritonitis model. ICR mice (female, 22-24 g, Charles River) were immunosuppressed by cyclophosphamide as described above. At day 0, MRSA ATCC 33591 ($1\times10^8$ CFU/mL in saline, 0.1 mL bacteria suspension per injection) was inoculated through i.p. injection, and the infected mice were randomly divided into 4 groups (n=5). 1 h after the infection, a single dose of different treatments was given through i.v. injection. 12 h after the inoculation, the animals were euthanized by $CO_2$ asphyxiation and their main organs (kidneys, liver, spleen, lung) and ascites were collected. For taking the ascites sample, 3 mL PBS was given through i.p. injection, and the abdomen of the mice were gently massaged. Peritoneal fluid was then removed from the peritoneum by syringe. The organs and tissue were homogenized and CFU was determined by serial dilution and plating.

Histopathological Analysis. ICR mice with P. aeruginosa lung infection were prepared as described above and received 2 PDC treatments 1 h and 8 h after the infection. The mice were euthanized 1 week after the infection, and the main organs including lung, heart, liver, spleen and kidneys were collected for histopathological analysis. As for comparison, organs from healthy mice and mice infected by *P. aeruginosa* but without treatment (euthanized 1 day after the infection) were also collected. The organs were embedded with optimum cutting temperature (OCT) compound (4583, Sakura, USA), frozen at −80° C. and sliced using a freezing microtome (−20° C.) with a thickness of 10 m. The sections were stained with hematoxylin and eosin (H&E) for histological examinations and imaged under an inverted microscope.

Statistical Analysis. Results are presented as mean standard deviation. Assignments to treatments and selections of fields of microscopic inspection were made at random. Differences between the experimental groups were assessed using a one-way ANOVA test followed by Tukey's post hoc comparisons test. For survival analysis, Kaplan-Meier curves were generated, and a Log-rank test was performed to find any overall differences between the survival curves. Analyses were performed on GraphPad Prism software. Significant differences between groups were indicated by *$p<0.05$, **$p<0.01$, respectively. $p<0.05$ was considered to be statistically significant in all analyses (95% confidence level).

Example 3—Biological Results and Discussion

In vivo biosafety is a serious consideration for antibacterial polymers. The cytotoxicity of the PDC and the Hex-Cys-DET polymer was tested on HEK 293 human embryonic kidney cell line via an MTT assay. As shown in FIG. 3B (2B), the Hex-Cys-DET based antibacterial materials revealed excellent biocompatibility. The neutralized polymer and PDC did not show any cytotoxicity at the concentration range we tested, while the positively-charged polymer and PDC only showed limited toxicity at a high concentration of 2,000 μg/mL, which was more than 100 times less toxic than the positive control polyhexanide is between 1 to 4, and antagonistic when it is above 4. Three bacterial strains, *E. coli* ATCC 25922, methicillin-resistant *S. aureus* (MRSA, ATCC 33591) and *P. aeruginosa* ATCC 27853 were chosen for this test as they are major human pathogens that have high tendencies of acquiring AMR. As shown in FIGS. 3D-F, the fractional inhibitory concentrations (FICs) of (free) streptomycin were significantly reduced when combined with (free) cationic polymer in all three bacteria strains. The FICI for *E. coli*, MRSA and *P. aeruginosa* were 0.375, 0.266 and 0.25, respectively, and indicates the interaction between these two components of the PDC proved synergistic.

The in vitro antibacterial activities of the polymer and PDC were evaluated at pH 7.4 and pH 6.0, mimicking the normal physiological condition and the infected tissue microenvironment, respectively, using the broth microdilution method. Both positively-charged and neutralized PDCs were evaluated. As shown in FIGS. 3G-I, PDCs exhibited much higher antibacterial efficacy compared with their corresponding polymers, leading to 4-8 fold reduction in minimum inhibitory concentration (MIC). As expected, DMA modification reduced cytotoxicity of the polymer to mammalian cells, but impaired the polymer's capability in disrupting bacterial membrane, leading to an increase of MIC for both the PDC and the polymer. Unlike the positively-charged PDC and polymer, where MICs were unaffected by pH variation, the neutralized PDCs and polymer performed significantly better at pH 6.0 than at 7.4, as their positive charge is unmasked quickly in acidic pH. The antibacterial property of the polymers and PDCs against a broad spectrum of microbes were tested and shown in Table 1. At pH 6.0 mimicking the inflammatory microenvironment, the MICs of the neutralized PDC ranged from 2.5 to 40 g/mL. The superior antibacterial efficacy for both Gram-negative and Gram-positive microorganisms demonstrates broad-spectrum activity of the PDC.

TABLE 1

Biological properties of the polymers and PDCs

| | MIC (μg/ml) | | | | | | HEK293 |
|---|---|---|---|---|---|---|---|
| | *E. coli* (DH5 alpha) | *E. coli* (ATCC 25922) | *S. aureus* (Newman) | *S. aureus* (MRSA ATCC33591) | *P. aeruginosa* (ATCC 27853) | *M. smegmatis* ($MC^2$ 155) | IC50 (μg/ml) |
| Streptomycin | 8 | 8 | 16 | 16 | 16 | 0.5 | — |
| Positively-charged polymer | 80 | 80 | 40 | 80 | 160 | 20 | >2000 |
| Positively-charged PDC | 20 | 20 | 10 | 20 | 20 | 1.25 | >2000 |
| Neutralized polymer (pH 7.4) | 640 | 640 | 320 | 640 | >1280 | 80 | >2000 |
| Neutralized polymer (pH 6.0) | 160 | 160 | 80 | 160 | 640 | 40 | — |
| Neutralized PDC (pH 7.4) | 80 | 80 | 80 | 160 | 160 | 20 | >2000 |
| Neutralized PDC (pH 6.0) | 20 | 20 | 20 | 40 | 40 | 2.5 | — |
| PHMB | 10 | 10 | 10 | 10 | 40 | 5 | 11.9 |

(PHMB), a commercially available cationic polymer that is widely used as a broad-spectrum antiseptic. Hemolysis assays carried out with human red blood cells were also used to evaluate the biocompatibility of the polymer and PDC. Similar to the MTT results, the neutralized polymer and PDC did not show any hemolytic activity while the positively-charged polymer and PDC only induced hemolysis at a high level of 10 mg/mL.

The synergistic effect between the cationic polymer and streptomycin were investigated using a checkerboard dilution assay and evaluated their fractional inhibitory concentration index (FICI). The interaction between the two components is considered synergistic when the FICI is less than 0.5; additive when it is between 0.5 to 1, indifferent when it The low MICs when compared with the results of the MTT and hemolysis assays, suggest superior therapeutic index. The HC50 (polymer concentration that induces 50% hemolysis) to MIC ratio was over 250 for *P. aeruginosa* and over 4,000 for *M. smegmatis*, which were significantly higher than those of many host defense peptides and antibacterial cationic polymers.

The FICI of the two components in the PDC (i.e., the antibiotic and polymer as tethered together) were assessed and found to be 0.362, 0.475 and 0.306, for *E. coli*, *S. aureus* and *P. aeruginosa*, respectively. Notably, the PDC showed the highest synergy in *P. aeruginosa*, a species that constitutively expresses efflux pumps (e.g., MexAB-OprM) and therefore exhibits strong intrinsic resistance. This finding suggests PDC effectively enhances bacteria membrane permeability and bypasses the efflux pumps of the bacteria.

Confocal laser scanning microscopy (CLSM) was employed to study the colocalization of the PDC and the bacteria. In the experiment, bacteria were visualized as green (acridine orange dye) and the PDC as red. The neutralized PDC tagged with a Cy5 fluorophore was incubated with the pathogens at different pH and time points. At pH 7.4, both at 10 and 60 min post-incubation, little PDC was shown to be attached to the bacteria. At pH 6.0, the red fluorescence increased dramatically after 60 min incubation in all three bacteria strains, suggesting a large amount of PDC adhered to the bacteria.

To further investigate the antibacterial mechanism and efficacy, *E. coli* was treated with the polymer and PDC and stained with a live/dead assay using AO (green fluorescence labeled live cells) and ethidium bromide (EB, red fluorescence, labeled dead cells) staining to monitor the cell survival. The resulting micrographs showed the positively-charged polymer induced significant cell death within 0.5 h, while the masked PDC showed a much delayed and pH-dependent bactericidal effect. Remarkably, the *E. coli* treated with masked polymer and PDC were stained with EB in pH 6.0 solution 3 h after the treatment. By contrast, the bacteria treated with streptomycin alone had little EB infiltration at 3 h. The AO/EB staining result demonstrated a quick membrane disruption effect induced by the cationic polymer, which facilitated the EB influx into the cell within a short time.

Figure 4:
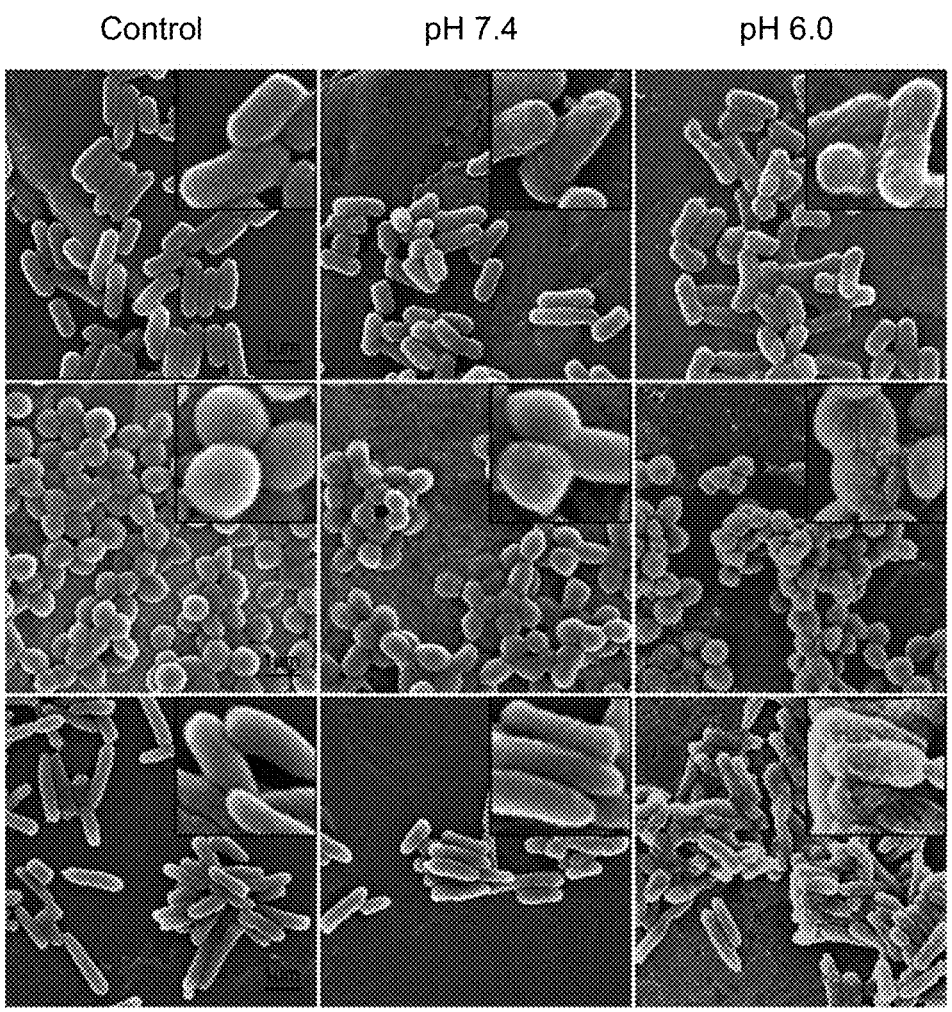
FIG. 4 shows SEM images of the bacteria treated with the PDC at pH 7.4 and 6.0 compared to untreated control. The arrows identify the defect on the bacteria cell wall and membrane induced by PDC incubation.

The cationic polymer induced membrane disruption was directly observed through scanning electron microscopy (SEM). Three bacterial strains, *E. coli*, MRSA and *P. aeruginosa* were treated with the PDC at both pH 7.4 and 6.0 (FIG. 4). Compared with the untreated bacteria that had a clear and smooth boundary, all three strains treated with PDC at pH 6.0 showed severe membrane disruption and deformation, again demonstrating that the cationic polymer effectively compromises the bacterial wall/membrane, thereby enhancing the permeability of the antibiotics.

Biofilm formation by bacteria can exacerbate AMR by building up extracellular polymeric substances (EPS) that increase antibiotic resistance by more than 1000-fold. To investigate the antibiofilm activity of the PDC, pathogen biofilms were treated with serial diluted PDC, and the biofilms stained with crystal violet for quantification. As shown in FIGS. 5A-C, *E. coli* and MRSA biofilms are extremely resistant free streptomycin, with more than 50% of their biofilms remaining when exposed to 512 µg/mL free streptomycin for 24 h. PDC significantly sensitized the antibiotic in eliminating biofilms, and it eliminated 75% of biofilms for both strains when the streptomycin concentration was 16 µg/mL. More than 90% of the MRSA biofilm was removed at an equivalent of 32 µg/mL streptomycin in acidic conditions. In the case of *P. aeruginosa* biofilm, free streptomycin reduced 75% of the biofilm at 256 µg/mL streptomycin, while PDC removed 96% of the biofilm at the same streptomycin concentration.

Biofilm penetration by PDC was investigated. Biofilms formed by *E. coli* ATCC 25922, *S. aureus* ATCC 33591, *P. aeruginosa* ATCC 27853 were incubated with Cy5 tagged neutralized PDC (red) at pH 6.0 for 30 min and 2 h, and then stained with AO (green) and visualized by CLSM. The resulting micrographs (not shown) indicate that PDC was mainly distributed on the surface of the biofilms at 30 min, but infiltrated into the entire biofilm after 2 h because the PDC can effectively penetrate through the biofilm after it recovered positive charge in the acidic microenvironment.

Continuous use of antibiotics can drive the selection of drug-resistant pathogens and lead to AMR. To explore whether the PDC would develop AMR in the same way as free antibiotic, *E. coli* was incubated in a sub-lethal dose of streptomycin, PDC, and polymer (0.5 MIC) for 20 passages (FIG. 5D). Free streptomycin quickly induced strong resistance and led to a 10-fold increase in MIC after 20 passages. In comparison, the neutralized polymer and PDC caused significantly lower and delayed resistance, with only a 2-fold increase in MIC.

Bacteria such as *M. tuberculosis* and *S. aureus* can invade and survive in macrophage and other non-phagocytic cells, thereby eluding antibiotic attacks since mammalian cells can reject most of the antibiotics. Those intracellular pathogens can lead to chronic and recurrent infections, spread infections throughout the body, and cause clinical failure. PDC is a desirable platform for eliminating intracellular infections, since the positively-charged PDC has a high trend of being internalized by mammalian cells, and releases the antibiotic in the acidic endosomal environment. To prove this, Raw 264.7 macrophage was infected with *S. aureus* or *P. aeruginosa*, and then treated with free streptomycin and PDC. As shown in FIGS. 5E-5F, PDC at both pH 7.4 and 6.0 enhanced the antibacterial efficacy especially for treating intracellular *P. aeruginosa*, in which free streptomycin did not show much therapeutic efficacy. The PDC revealed better performance in acidic media since it could recover its positive charge and enter the cell more efficiently.

Figure 6B:
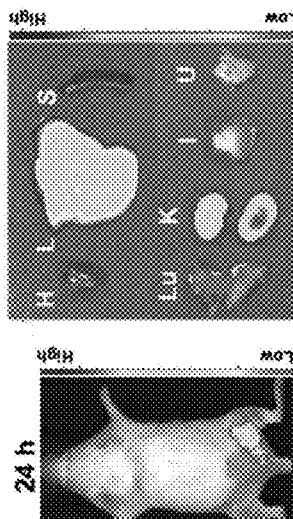
Figure 6A:
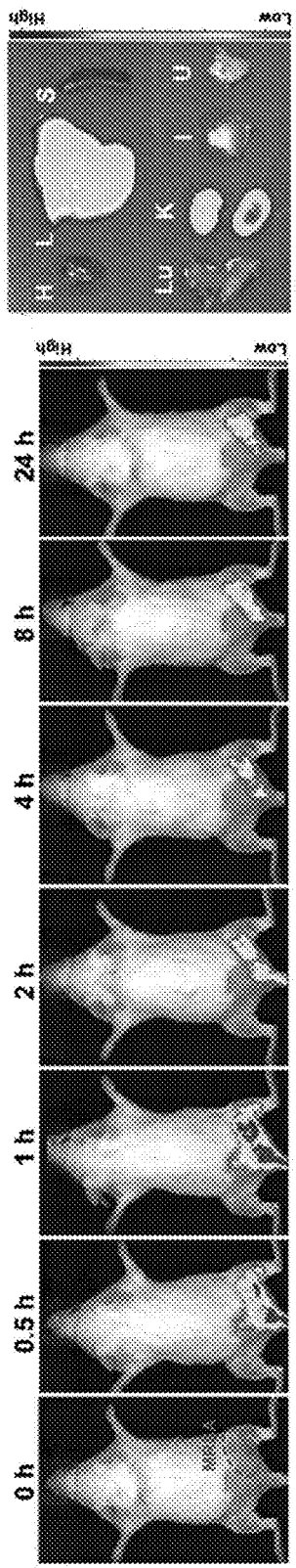
Figure 6E:
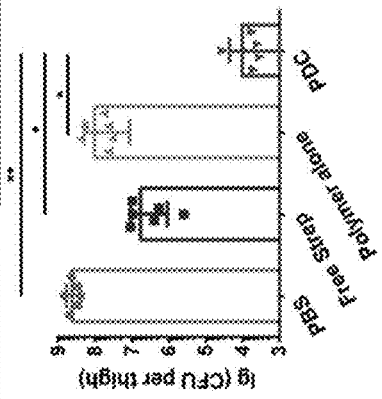
Figure 6D:
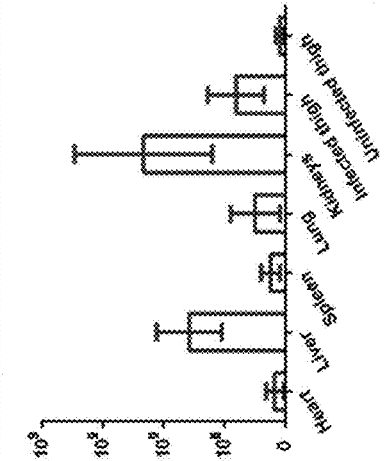
Figure 6C:
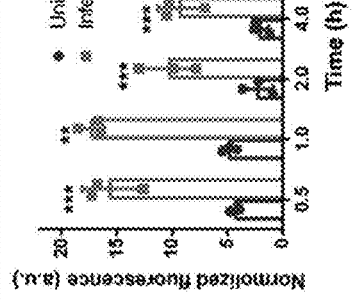

Infection can cause local inflammation which leads to endothelial hyperpermeability as well as the accumulation of macromolecules through the EPR effect. Under an acidic microenvironment, the neutralized PDC recovers its positive charge and markedly reduces its migration ability, thereby further enhancing its retention in the infected tissue. To validate this concept, ICR mice were infected with MRSA in the right thigh and intravenously administrated Cy5 tagged PDC to observe its in vivo distribution through an IVIS system. The PDC exhibited significant and persistent accumulation in the MRSA infected thigh, but not the normal thigh, throughout 24 h post-injection we monitored (FIG. 6A). Semiquantitative analysis (FIG. 6C) confirmed the observation in the image and showed a 6.8 times difference in PDC accumulation between the two thighs at 24 h post-injection. The mice were sacrificed after 24 h and their organs and tissues were collected for ex vivo imaging. As shown in FIGS. 6B and 6D, kidneys and liver had the highest PDC distribution as expected due to their role in eliminating xenobiotic substances. Beyond these two organs, the MRSA infected thigh exhibited the highest PDC accumulation surpassing all other organs and tissues, and demonstrating the infection targeting capability of the PDC.

The in vivo antibacterial efficacy of the PDC was first evaluated in an *E. coli* thigh infection model. ICR mice were intramuscularly injected with *E. coli* ATCC 25922 ($1 \times 10^7$ CFU per thigh) on both thighs and treated with streptomycin (5 mg/kg), PDC (equivalent of 5 mg streptomycin/kg), the polymer (50 mg/kg) or PBS through intravenous injection 1 h after the infection. The animals were euthanized after 24 h and both thighs were collected for bacterial quantification. The PDC exhibited a significantly higher antibacterial efficacy than free streptomycin alone, leading to more than 4 orders of reductions in CFU (FIG. 6E).

We then investigated the therapeutic efficacy of the PDC in treating *P. aeruginosa* lung infections, which is a pathogen that possesses strong intrinsic resistance to various antibacterial agents and leads to severe healthcare-associated infections (e.g., nosocomial pneumonia) in immunocompromised patients. The antibacterial efficacy of the PDC was evaluated on a *P. aeruginosa* lung infection mice model. The immunosuppressed mice were inoculated with $5 \times 10^6$ CFU *P. aeruginosa* through intratracheal injection to mimic hospital-acquired pneumonia, and the therapeutic efficacy for each treatment was evaluated by monitoring the bacterial burden in lungs (FIG. 6F) and the survival curve (FIG. 6G). The mice injected with PDC possessed the lowest bacterial burden in their lungs and all of the PDC treated mice survived after the treatment. In contrast, mice treated with PBS all died within 4 days, and only 40% of mice were rescued by free streptomycin.

We further evaluated the PDC's effectiveness in treating MRSA induced peritonitis, since MRSA is one of the major AMR pathogens with high morbidity and mortality. Mice were infected with a lethal dose of MRSA ($1 \times 10^7$ CFU per mouse) through i.p. injection and received different treatments through i.v. injection 1 h after the infection. 12 h after the inoculation, tissue and organs including ascites, liver, kidneys, lung and spleen were collected for bacterial quantification (FIGS. 6H-L). The PDC improved the therapeutic efficacy in all tissues and organs we tested compared with free streptomycin or free polymer, leading to 3 to 4 orders of magnitudes reduction of CFU in all organs. The in vivo antibacterial efficacy studies conducted in three different infectious mice models demonstrated the PDC's superior capability in overcoming AMR infections for both Gram-negative and Gram-positive pathogens.

EQUIVALENTS

While certain embodiments have been illustrated and described, a person with ordinary skill in the art, after reading the foregoing specification, can effect changes, substitutions of equivalents and other types of alterations to the PDCs of the present technology or derivatives, prodrugs, or pharmaceutical compositions thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, conjugates, reagents, compounds, compositions, labeled compounds or biological systems, which can, of course, vary. All methods described herein can be performed in any suitable order unless otherwise indicated herein or otherwise clearly contradicted by context. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof. No language in the specification should be construed as indicating any non-claimed element as essential.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified. Moreover, use of any of the foregoing terms in the description with respect to a particular element or embodiment also contemplates the use of any of the other terms. For example, use of "comprise" with respect to one element or embodiment will also be understood to disclose use of "consisting essentially of" or "consists of" in respect of the same element or embodiment and vice versa.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the technology. This includes the generic description of the technology with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member, and each separate value is incorporated into the specification as if it were individually recited herein.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims, along with the full scope of equivalents to which such claims are entitled.

What is claimed is:

1. A polymer-drug conjugate comprising:
a polymer comprising a plurality of masked cationic functional groups wherein the masked cationic functional groups are converted in aqueous solution to free cationic functional groups faster at a pH below 7 than a pH above 7; wherein
the cationic functional groups are masked as either an uncharged functional group or by an ion pair with a neighboring anionic functional group attached to the polymer; and
an antibiotic drug linked to the cationic polymer by a pH-sensitive linker that releases the drug faster in aqueous solution at a pH value selected from a range of 4.5 to 7 compared to a pH value above 7; and wherein
the polymer comprises one or more disulfide bonds in a backbone of the polymer;
the plurality of masked cationic functional groups comprise amide, amine, amidine, guanidine, ammonium, amidinium, and/or guanidinium functional groups; and
the pH-sensitive linker is selected from the group consisting of hydrazone, 2,3-dimethyl maleic acid ester and/or amide, imine, ketal, acetal, and phenyl boronic acid and ester.

2. The polymer-drug conjugate of claim 1, wherein one or more of the plurality of masked cationic functional groups are present in a backbone of the polymer, in one or more side-chains of the polymer, or in both the backbone and one or more side-chains of the polymer.

3. The polymer-drug conjugate of claim 1, wherein one or more of the plurality of masked cationic functional groups of the polymer are present in one or more side-chains of the polymer.

4. The polymer-drug conjugate of claim 1, wherein the neighboring anionic functional group attached to the polymer is a carboxyl or carboxylate group.

5. The polymer-drug conjugate of claim 4, wherein the anionic functional group is attached to the polymer as a 2,3-dimethylmaleic acid or cis-aconitic acid through an amide group.

6. The polymer-drug conjugate of claim 1, wherein the polymer is selected from the group consisting of polyurea, polyurethane, polypeptide, polyester, poly(β-amino ester) and combinations thereof.

7. The polymer-drug conjugate of claim 1, wherein the polymer has a weight average molecular weight of 1 kD to 40 kD.

8. The polymer-drug conjugate of claim 1, wherein the polymer has a weight average molecular weight of 6 kD to 8 kD.

9. The polymer-drug conjugate of claim 1, wherein the polymer comprises repeating subunits comprising an unbranched $C_{2-12}$ alkylene chain.

10. The polymer-drug conjugate of claim 1, wherein the polymer is polyurea comprising repeating subunits comprising an unbranched $C_{2-12}$ alkylene chain and comprising disulfide bonds.

11. The polymer-drug conjugate of claim 10, wherein the repeating subunits comprise a cystine group.

12. The polymer-drug conjugate of claim 10, wherein the repeating subunits comprise a cystine group further comprising masked cationic functional groups.

13. The polymer-drug conjugate of claim 12 wherein the masked cationic functional group comprises diethyltriamine attached to 2,3-dimethyl maleic acid via an amide bond.

14. The polymer-drug conjugate of claim 1, wherein the polymer comprises a subunit having one or two of the following structures:

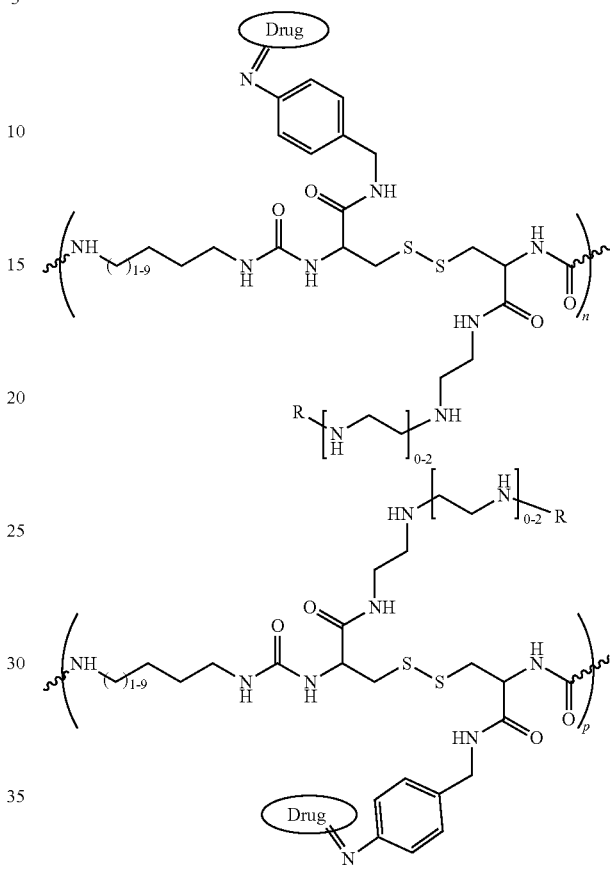

wherein
one or both of n and p are independently an integer of 1-70;
R is H or —C(O)C(CH$_3$)=C(CH$_3$)C(O)OH; and
Drug is the antibiotic drug.

15. The polymer-drug conjugate of claim 14, wherein the polymer further comprises a subunit having the following structure:

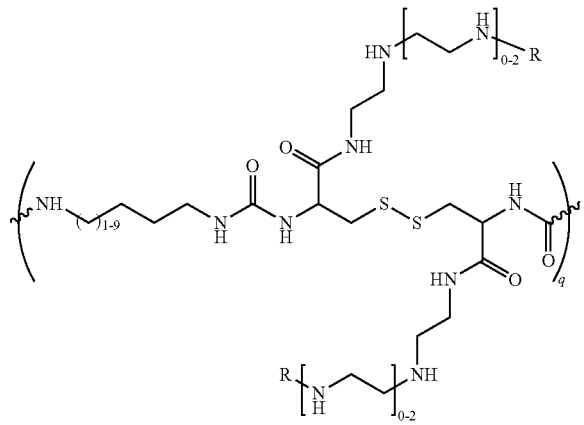

wherein
one or both of n and p are independently an integer of 1-70;
q is 0-69, provided n+p+q=2-70; and
R is H or —C(O)C(CH$_3$)=C(CH$_3$)C(O)OH.

16. The polymer-drug conjugate of claim 1, wherein the antibiotic drug is one or more of streptomycin, clindamycin, gentamycin, ciprofloxacin, vancomycin, sulfathiazole, spectinomycin, roxithromycin, sisomicin, novobiocin, isoniazide, rifampicin, clarithromycin, salinomycin and roxithromycin.

17. A pharmaceutical composition comprising a polymer-drug conjugate of claim 1 and a pharmaceutically acceptable carrier or excipient.

18. A method of treatment comprising administering to a subject suffering from a bacterial infection an effective amount of a polymer-drug conjugate of claim 1.

19. The method of claim 18 wherein the bacterial infection comprises a drug-resistant bacterial strain and/or a bacterial biofilm.

20. The method of claim 18 wherein the subject is infected with one or more of *E. coli*, MRSA, and *P. aeruginosa*.

21. The method of claim 18, wherein the subject is human.

22. A polymer-drug conjugate comprising:
a polymer comprising a plurality of cationic functional groups selected from ammonium, amidinium, and/or guanidinium functional groups; and
an antibiotic drug linked to the cationic polymer by a pH-sensitive linker that releases the drug faster in aqueous solution at a pH value selected from a range of 4.5 to 7 compared to a pH value above 7;
wherein
the polymer comprises one or more disulfide bonds in a backbone of the polymer; and
the pH-sensitive linker is selected from the group consisting of hydrazone, 2,3-dimethyl maleic acid ester and/or amide, imine, ketal, acetal, and phenyl boronic acid and ester.

* * * * *